(12) United States Patent
Takagi (10) Patent No.: US 10,842,414 B2
(45) Date of Patent: Nov. 24, 2020

(54) INFORMATION PROCESSING DEVICE, INFORMATION PROCESSING METHOD, PROGRAM, AND WATCHING SYSTEM

(71) Applicant: Sony Corporation, Tokyo (JP)

(72) Inventor: Yoshimitsu Takagi, Tokyo (JP)

(73) Assignee: Sony Corporation, Tokyo (JP)

( * ) Notice: Subject to any disclaimer, the term of this patent is extended or adjusted under 35 U.S.C. 154(b) by 99 days.

(21) Appl. No.: 16/088,619

(22) PCT Filed: May 11, 2017

(86) PCT No.: PCT/JP2017/017815
§ 371 (c)(1),
(2) Date: Sep. 26, 2018

(87) PCT Pub. No.: WO2017/203986
PCT Pub. Date: Nov. 30, 2017

(65) Prior Publication Data
US 2019/0104972 A1 Apr. 11, 2019

(30) Foreign Application Priority Data

May 25, 2016 (JP) .................................. 2016-103918

(51) Int. Cl.
*A61B 5/11* (2006.01)
*G06K 9/00* (2006.01)
(Continued)

(52) U.S. Cl.
CPC .......... *A61B 5/1128* (2013.01); *A61B 5/0077* (2013.01); *A61B 5/1113* (2013.01);
(Continued)

(58) Field of Classification Search
CPC .. A61B 5/1128; G06K 9/00771; G08B 25/04; G08B 25/00; G08B 21/02; H04N 7/188
(Continued)

(56) References Cited

U.S. PATENT DOCUMENTS

2013/0301882 A1* 11/2013 Kawaguchi ........ G06K 9/00335
382/103

FOREIGN PATENT DOCUMENTS

JP 2001-243472 A 9/2001
JP 2008-225803 A 9/2008
(Continued)

OTHER PUBLICATIONS

English Translation of "Tanaka, Monitor, Jul. 30 2015" in pdf form (Year: 2015).*

*Primary Examiner* — Ayodeji O Ayotunde
(74) *Attorney, Agent, or Firm* — Michael Best & Friedrich LLP (57) ABSTRACT

The present disclosure relates to an information processing device, an information processing method, a program, and a watching system that enable determination of a specific region, such as the region occupied by a bed, in accordance with a captured image.
An information processing device as an aspect of the present disclosure includes: a moving object detection unit that detects a moving object in a captured image; a stay area information holding unit that holds stay area information indicating the position of the moving object detected in the captured image; a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map. The present disclosure can be applied to watching systems installed in elderly care facilities and the like, for example.

22 Claims, 7 Drawing Sheets (51) Int. Cl.
*G06T 7/215* (2017.01)
*G08B 25/04* (2006.01)
*G08B 25/00* (2006.01)
*G08B 21/02* (2006.01)
*G08B 21/04* (2006.01)
*H04N 7/18* (2006.01)
*G06T 7/246* (2017.01)
*A61B 5/00* (2006.01)

(52) U.S. Cl.
CPC ........ *A61B 5/6889* (2013.01); *G06K 9/00335* (2013.01); *G06K 9/00771* (2013.01); *G06T 7/215* (2017.01); *G06T 7/246* (2017.01); *G08B 21/02* (2013.01); *G08B 21/0407* (2013.01); *G08B 21/0476* (2013.01); *G08B 25/00* (2013.01); *G08B 25/04* (2013.01); *H04N 7/188* (2013.01); *A61B 5/1115* (2013.01); *A61B 5/1117* (2013.01); *A61B 2503/08* (2013.01); *A61B 2505/07* (2013.01); *A61B 2576/00* (2013.01); *G06T 2207/30196* (2013.01); *G06T 2207/30232* (2013.01); *H04N 7/183* (2013.01)

(58) Field of Classification Search
USPC .......................................................... 382/103
See application file for complete search history.

(56) References Cited

FOREIGN PATENT DOCUMENTS

| | | | |
|---|---|---|---|
| JP | 2009-239507 | A | 10/2009 |
| JP | 2014-182409 | A | 9/2014 |
| JP | 2015-119898 | A | 7/2015 |
| JP | 2015-138427 | A | 7/2015 |
| JP | 2015138427 | A * | 7/2015 |

* cited by examiner

INFORMATION PROCESSING DEVICE, INFORMATION PROCESSING METHOD, PROGRAM, AND WATCHING SYSTEM

TECHNICAL FIELD

The present disclosure relates to an information processing device, an information processing method, a program, and a watching system, and more particularly, to an information processing device, an information processing method, a program, and a watching system that are installed in an elderly care facility or the like and can be suitably used to watch the states of care-receivers, for example.

BACKGROUND ART

In an elderly care facility or the like, for example, a watching system formed with a camera and the like is installed in the rooms of care-receivers, to watch the states (such as sleeping, waking up (hereinafter also referred to as leaving the bed), falling, and leaving the room) of the care-receivers.

Conventionally, to install a watching system so that the watching system can correctly detect a care-receiver leaving the bed, it is necessary to adjust the orientation of the camera while checking a captured image, and manually designate the region of the bed in the captured image on the monitor, prior to the start of operation of the watching system (see Patent Document 1, for example).

CITATION LIST

Patent Document

Patent Document 1: Japanese Patent Application Laid-Open No. 2014-182409

SUMMARY OF THE INVENTION

Problems to be Solved by the Invention

The above mentioned task of adjusting the orientation of the camera and manually designating the region of the bed is very troublesome in an elderly care facility or the like that has a large number of rooms. Also, in a case where the room layout is changed, a similar task is again required.

The present disclosure is made in view of such circumstances, and aims to estimate a specific region such as a bed in accordance with a captured image formed by imaging the entire room from above.

Solutions to Problems

An information processing device as a first aspect of the present disclosure includes: a moving object detection unit that detects a moving object in a captured image; a stay area information holding unit that holds stay area information indicating the position of the moving object detected in the captured image; a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map.

The stay frequency map generation unit may extract, from time-series stay area information being held, the stay area information corresponding to a predetermined time period determined in accordance with time information, and generate a stay frequency map by combining the extracted stay area information.

The time information includes a time schedule of a facility in which the information processing device is being used.

The stay frequency map generation unit may extract, from time-series stay area information being held, the stay area information corresponding to a predetermined time period determined in accordance with moving object information about the moving object, and generate a stay frequency map by combining the extracted stay area information.

The moving object information may include the respiration rate and/or the heart rate of a living body as the moving object.

The information processing device as the first aspect of the present disclosure may further include a moving object information acquisition unit that acquires the moving object information by sensing the imaging range of the captured image.

The information processing device as the first aspect of the present disclosure may further include an imaging unit that forms the captured image.

The information processing device as the first aspect of the present disclosure may further include an illumination unit that illuminates the imaging range of the captured image with visible light and/or invisible light.

The information processing device as the first aspect of the present disclosure may further include a behavior recognition unit that performs behavior recognition on the moving object, in accordance with the captured image and the specific region in the captured image.

The information processing device as the first aspect of the present disclosure may further include a reporting unit that reports a result of recognition of a behavior of the moving object.

An information processing method as the first aspect of the present disclosure is an information processing method implemented in an information processing device, and causes the information processing device to carry out: a moving object detection step of detecting a moving object in a captured image; a stay area information holding step of holding stay area information indicating the position of the moving object detected in the captured image; a stay frequency map generation step of extracting the stay area information corresponding to a predetermined time period from time-series stay area information being held, and generating a stay frequency map by combining the extracted stay area information; and a specific region determination step of determining a specific region having a high stay frequency regarding the moving object, in accordance with the generated stay frequency map.

A program as the first aspect of the present disclosure causes a computer to function as: a moving object detection unit that detects a moving object in a captured image; a stay area information holding unit that holds stay area information indicating the position of the moving object detected in the captured image; a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map.

In the first aspect of the present disclosure, a moving object in a captured image is detected, stay area information indicating the position of the moving object detected in the captured image is held, the stay area information corresponding to a predetermined time period is extracted from time-series stay area information being held, a stay frequency map is generated by combining the extracted stay area information, and a specific region with a high stay frequency regarding the moving object is determined in accordance with the generated stay frequency map.

A watching system as a second aspect of the present disclosure includes: an imaging unit that forms a captured image; an illumination unit that illuminates the imaging range of the imaging unit with visible light and/or invisible light; a moving object detection unit that detects a moving object in a captured image; a stay area information holding unit that holds stay area information indicating the position of the moving object detected in the captured image; a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map.

In the second aspect of the present disclosure, a captured image is formed, a moving object in the captured image is detected, stay area information indicating the position of the moving object detected in the captured image is held, the stay area information corresponding to a predetermined time period is extracted from time-series stay area information being held, a stay frequency map is generated by combining the extracted stay area information, and a specific region with a high stay frequency regarding the moving object is determined in accordance with the generated stay frequency map.

Effects of the Invention

According to the first and second aspects of the present disclosure, it is possible to estimate a specific region, such as a bed, in accordance with a captured image.

MODE FOR CARRYING OUT THE INVENTION

The following is a detailed description of the best mode for carrying out the present disclosure (hereinafter referred to as the embodiment), with reference to the drawings.

Watching System as an Embodiment of the Present Disclosure

Figure 1:
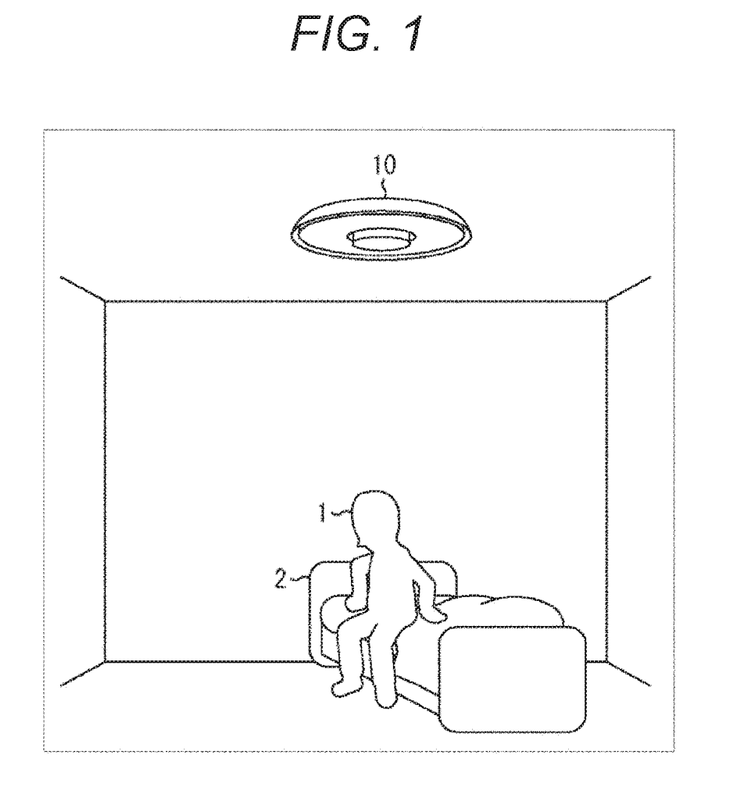
FIG. 1 is a diagram showing an example of installation of a watching system to which the present disclosure is applied.

FIG. 1 is a diagram showing an example of installation of a watching system as an embodiment of the present disclosure. The watching system 10 is incorporated into a ceiling light attached to the ceiling or the like of each room in an elderly care facility or the like, for example. The watching system 10 captures an image of the inside of a room from a higher viewpoint, detects the behavior/state of a moving object (a care-receiver 1 in this case) in accordance with the resultant captured image, and reports the detection result to the caregiver side. To sense behaviors and states, the watching system 10 has the function of determining a specific region such as a bed 2 on which the moving object often stays.

Note that the entire watching system 10 may be incorporated into the ceiling light, or only part of the watching system 10 (an imaging unit 11, an illumination unit 12, a moving object information sensing unit 19, and the like, which will be described later) may be incorporated into the ceiling light. Alternatively, the entire or part of the watching system 10 may be installed, separately from the ceiling light, in the ceiling, an upper portion of a wall surface, or the like.

Figure 2:
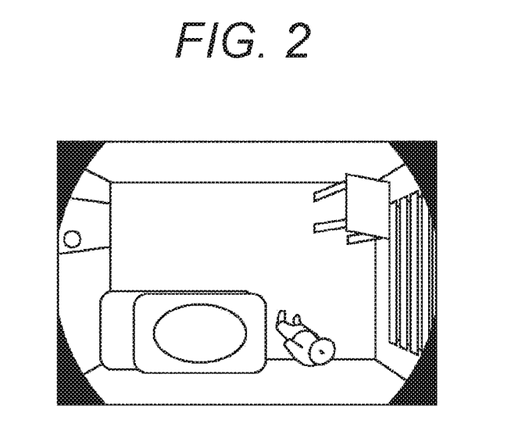
FIG. 2 is a diagram showing an example of a captured image.

FIG. 2 shows an example of a captured image. As shown in this drawing, imaging is performed from the ceiling, so that the entire room falls within the imaging range. Furthermore, there are fewer obstacles in the view from the ceiling. Accordingly, it becomes easier to determine the position (two-dimensional coordinates) of the care-receiver in the room.

<Example Configuration of the Watching System 10>

Figure 3:
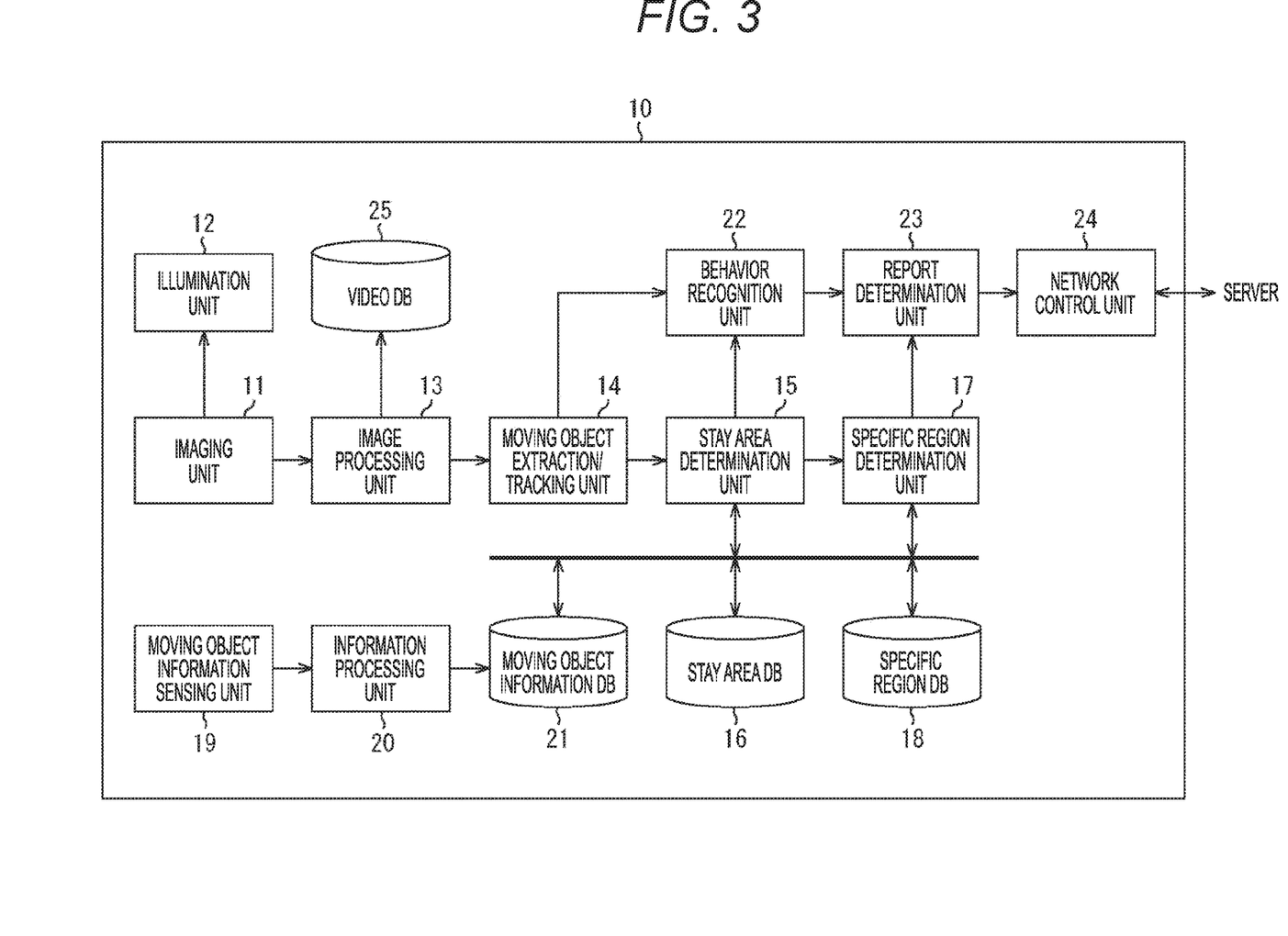
FIG. 3 is a block diagram showing an example configuration of the watching system.

FIG. 3 shows an example configuration of the watching system 10.

The watching system 10 includes an imaging unit 11, an illumination unit 12, an image processing unit 13, a moving object extraction/tracking unit 14, a stay area determination unit 15, a stay area database 16, a specific region determination unit 17, and a specific region database 18. The watching system 10 further includes a moving object information sensing unit 19, an information processing unit 20, a moving object information database 21, a behavior recognition unit 22, a report determination unit 23, a network control unit 24, and a video database 25.

The imaging unit 11 is formed with a digital camera or the like disposed in a ceiling light on the ceiling of a room as shown in FIG. 1, for example. The imaging unit 11 captures an image of the entire room from a higher viewpoint at a predetermined frame rate, and sequentially outputs the resultant data to the image processing unit 13. The illumination unit 12 is formed with an LED light or the like also serving as the ceiling light on the ceiling of the room as shown in FIG. 1, and illuminates the imaging range of the imaging unit 11 with visible light or invisible light (IR light).

The image processing unit 13 performs image processing, such as development, adjustment of gradation and color tone, a noise reduction process, distortion correction, and size conversion, on the image data obtained from the imaging unit 11, and outputs the resultant captured image to the subsequent stage.

The moving object extraction/tracking unit 14 extracts a moving object (specifically, a care-receiver in most cases) from the captured image, and tracks the moving object. The stay area determination unit 15 divides the inside of the imaging screen into a plurality of areas, and determines to which of the plurality of areas the coordinates of the extracted moving object belong. The stay area database 16 records and holds stay area information indicating in time series the area to which the coordinates of the moving object belong, which has been determined by the stay area determination unit 15.

The specific region determination unit 17 determines a specific region (the region occupied by a bed, for example) in the captured image, using time information and/or moving object information, as well as the stay area information.

Here, the time information refers to a time schedule or the like in the elderly care facility in which the watching system 10 is installed. Specifically, the time information includes information about the time periods for meals, bathing, sleeping, and the like. Moving object information refers to information about the heart rate, the respiration rate, and the like of the care-receiver obtained by sensing. The specific region database 18 records and holds the specific region determined by the specific region determination unit 17.

The moving object information sensing unit 19 acquires vital signs such as the heartbeat and the respiration of the moving object, which is a living body, by non-contact sensing using millimeter waves, microwaves, or the like. The information processing unit 20 performs predetermined information processing, to convert the unprocessed vital signs acquired by the moving object information sensing unit 19 into the moving object information about the heart rate, the respiration rate, and the like. The moving object information database 21 records and holds the converted moving object information in time series.

The behavior recognition unit 22 recognizes the behavior (such as sleeping, leaving the bed, falling, or leaving the room) of the moving object (a care-receiver in most cases) extracted from the captured image. The report determination unit 23 determines whether or not the result of the behavior recognition is a behavior or a state that needs to be reported. If it is determined that the result of the behavior recognition needs to be reported, the report determination unit 23 notifies the network control unit 24 of the determination result. The network control unit 24 is connected to a predetermined server in a wired or wireless manner, and, in accordance with the notification from the report determination unit 23, reports the behavior of the moving object to the predetermined server.

The video database 25 records and holds the captured image as necessary when an abnormality or the like is detected.

<Operation of the Watching System 10>

Figure 4:
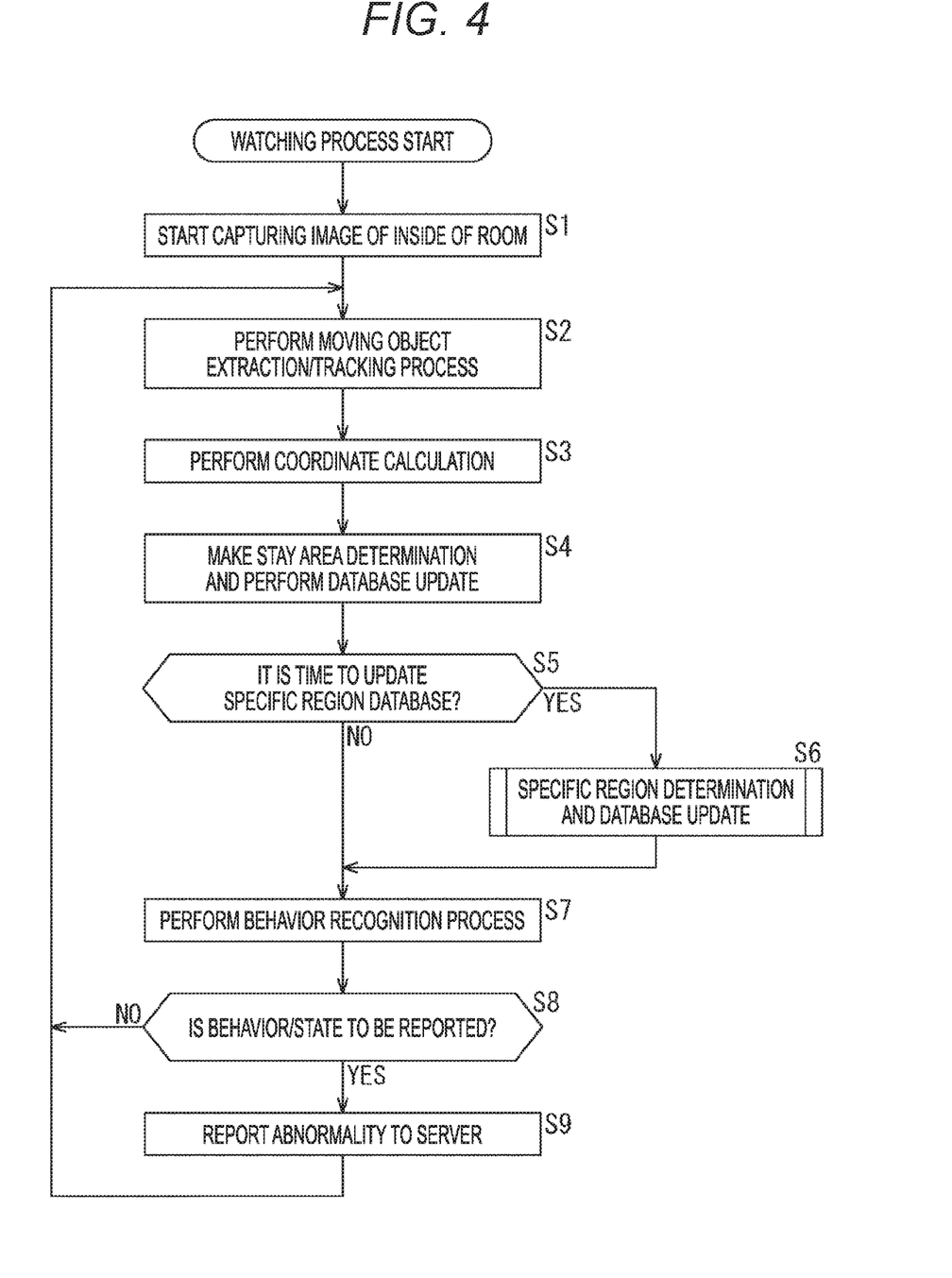
FIG. 4 is a flowchart for explaining the watching system.
Figure 5:
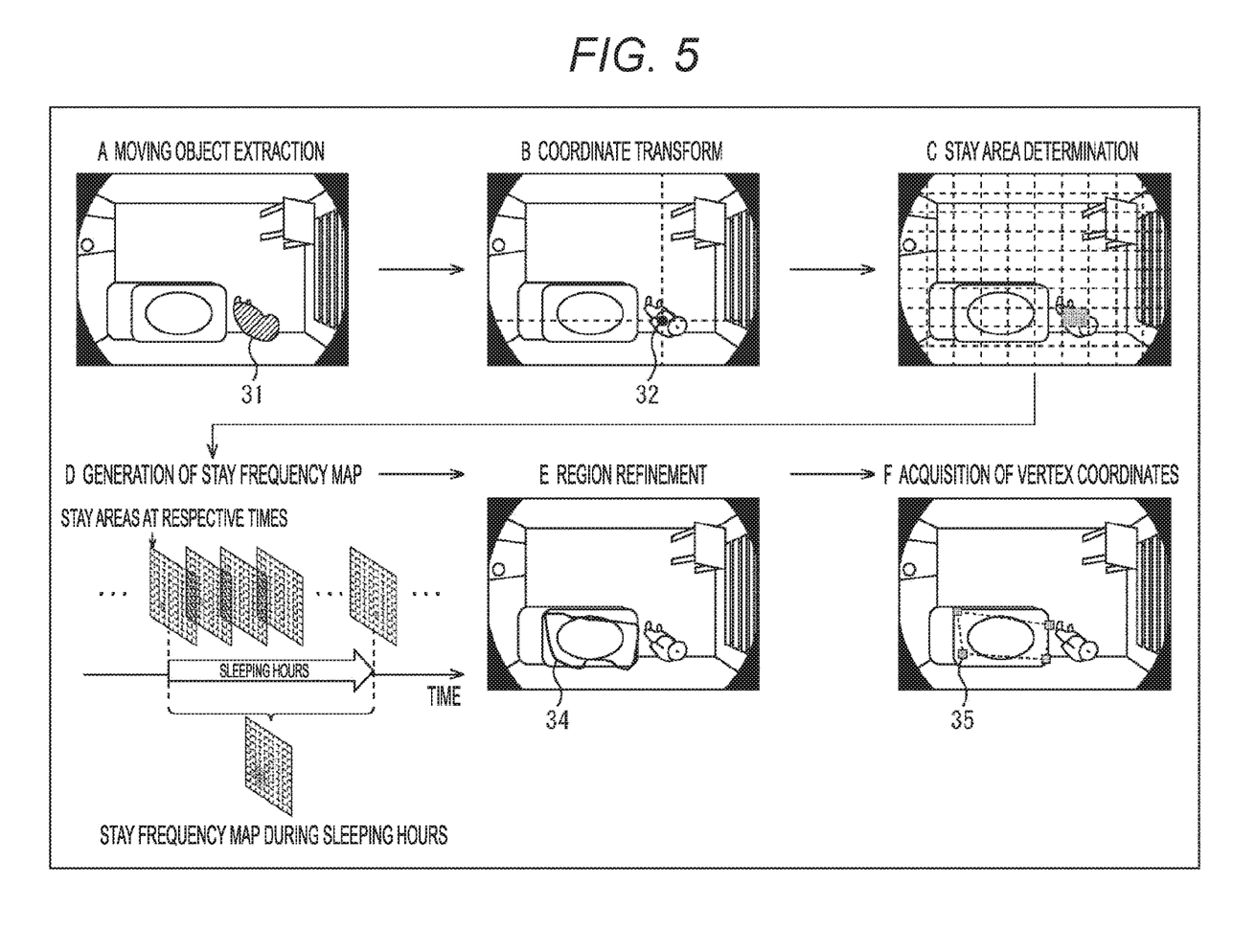
FIG. 5 is a diagram for explaining the watching system.

Next, operation of the watching system 10 is described. FIG. 4 is a flowchart for explaining a watching process to be performed by the watching system 10. FIG. 5 is a diagram for explaining the watching process.

In step S1, the imaging unit 11 starts capturing images of the inside of the room. In this step, the illumination unit 12 illuminates the inside of the room with visible light or invisible light (nighttime) as necessary. As a result, the image data obtained by the imaging performed by the imaging unit 11 is supplied to the image processing unit 13, and captured images are sequentially supplied from the image processing unit 13 to the moving object extraction/tracking unit 14.

In step S2, the moving object extraction/tracking unit 14 extracts a moving object (a care-receiver in most cases) region 31 from the time-series captured images, as shown in A of FIG. 5, and tracks the moving object. In step S3, the stay area determination unit 15 calculates the central coordinates 32 of the extracted moving object region 31, as shown in B of FIG. 5. In step S4, the stay area determination unit 15 determines to which area in the captured image the calculated central coordinates 32 of the moving object belong, as shown in C of FIG. 5, and causes the stay area database 16 to record and hold stay area information that is the determination result.

In step S5, the specific region determination unit 17 determines whether or not it is time to update the specific region database 18. If it is determined to be the update time, the process moves on to step S6. In this example, the time to update the specific region database 18 is set in advance, like once a day at 9 am, for example. Also, this update time can be changed by the user when the daily routine of the care-receiver changes. Note that, if it is determined not to be the update time in step S5, step S6 is skipped, and the process moves on to step S7.

In step S6, the specific region determination unit 17 performs a specific region determination process to determine a specific region in accordance with the stay area information recorded in the stay area database 16. Note that the specific region determination process will be described later in detail with reference to FIG. 6.

In step S7, the behavior recognition unit 22 performs behavior recognition to recognize the moving object moving from the specific region determined in step S6, such as a care-receiver leaving the bed, and outputs the result to the report determination unit 23. In step S8, the report determination unit 23 determines whether or not the result of the behavior recognition is a behavior or a state (such as falling or leaving the room, for example) that needs to be reported. If the result of the behavior recognition is determined to be a behavior or a state to be reported, the process moves on to step S9, and the network control unit 24 is notified of the determination result. In response to this notification, the network control unit 24 reports the behavior or the state of the moving object to the predetermined server. In accordance with this report, the server reports the behavior or the state of the care-receiver to the caregiver.

If it is determined in step S8 that the behavior or the state does not need to be reported, the process is returned to step S2, and the procedures thereafter are repeated.

Figure 6:
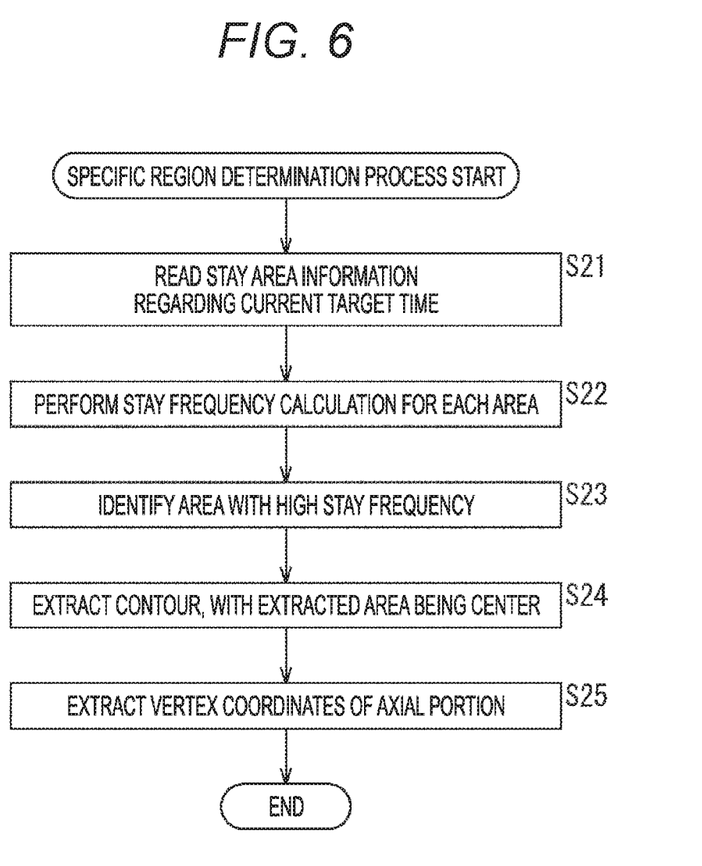
FIG. 6 is a flowchart for explaining a specific region determination process in detail.

Next, the above mentioned specific region determination process in step S6 is described in detail. FIG. 6 is a flowchart for explaining the specific region determination process in detail.

In step S21, the specific region determination unit 17 reads the stay area information regarding the current target time from the stay area database 16, as shown in D of FIG. 5. Here, in a case where the region occupied by a bed is determined to be the current target region, for example, the sleeping time period with the highest possibility of the moving object (a care-receiver) being on the bed is set as the current target time, in accordance with time information (the time schedule or the like in the elderly care facility) acquired in advance.

In step S22, the specific region determination unit 17 adds the stay area information regarding the current target time read in step S21 for each area, and generates a stay frequency map (a heat map) indicating the stay frequency for each area. In step S23, the specific region determination unit 17 identifies the area having a high stay frequency, in accordance with the generated stay frequency map.

In step S24, the specific region determination unit 17 performs refinement on the area in a predetermined range centered on the area specified as the area having a high stay frequency. Specifically, as shown in E of FIG. 5, the contour 34 of an object (assumed to be a bed in this case) existing in the area in the above range is extracted. In step S25, as shown in F of FIG. 5, the specific region determination unit 17 extracts the vertex coordinates of the contour 34 extracted in step S24. The area surrounded by the vertex coordinates extracted in this manner is determined to be a specific region.

In the specific region determination process described above, stay area information is selected in accordance with the time information, and a stay frequency map is generated and used in determining a specific region. Thus, a specific region can be determined more accurately with a smaller amount of calculation than in a case where a stay frequency map is generated from all the stay area information.

Figure 7:
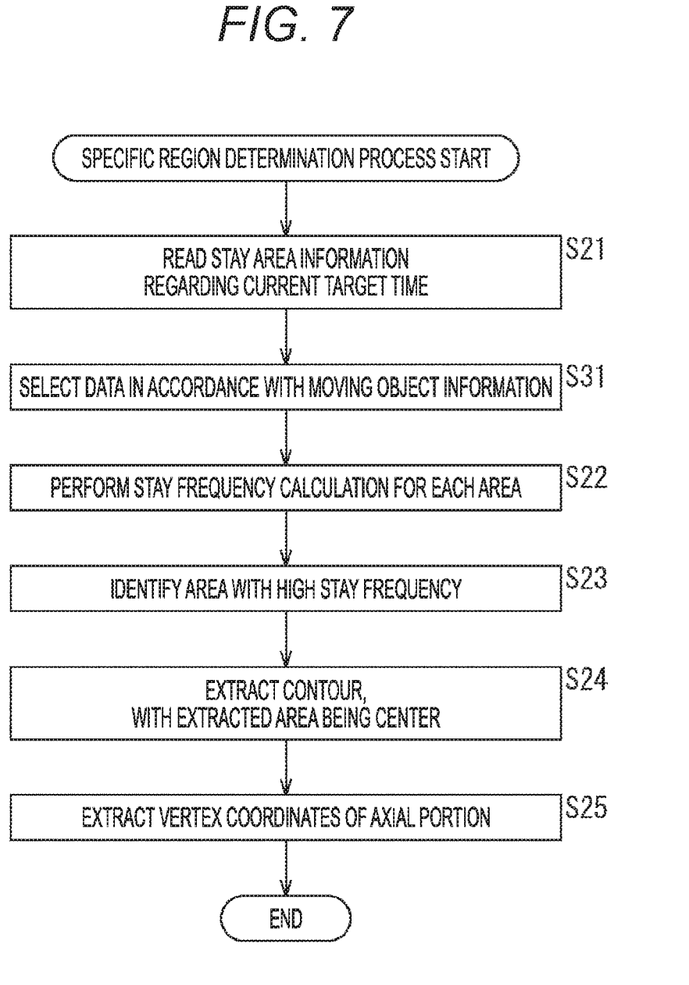
FIG. 7 is a flowchart for explaining a modification of the specific region determination process in detail.

FIG. 7 is a flowchart for explaining a modification of the above specific region determination process in detail. In the modification shown in FIG. 7, step S31 is added between step S21 and step S22 of the specific region determination process shown in FIG. 6.

In step S31, the specific region determination unit 17 acquires the moving object information (such as the heart rate and the respiration rate) about the care-receiver from the moving object information database 21, and, from the acquired moving object information, estimates the time period during which the care-receiver sleeps (the sleeping time period). Further, of the stay area information regarding the current target time read in step S21, the information belonging to the estimated sleeping time period is selected and is used in the next step S22.

In the above described modification, stay area information is selected in accordance with the time information and the moving object information, and is used in generating a stay frequency map. Accordingly, a specific region can be determined more accurately with a smaller amount of calculation than in the specific region determination process shown in FIG. 6.

Also, in the above described case, the region occupied by a bed is determined to be a specific region. However, the present disclosure can also be applied in cases where the region occupied by a dining table or the region occupied by a sofa placed in front of a television set is determined to be a specific region, for example.

In another example application, a stay frequency map may be generated or updated on a certain day of the week or at a certain time period of the day, for example, and, if a behavior or a state that departs from the stay frequency map is recognized, a report of an abnormality may be reported to the server.

Meanwhile, the above described series of processes may be performed by hardware or may be performed by software. Where the series of processes are to be performed by software, the program that forms the software is installed into a computer. Here, the computer may be a computer incorporated into special-purpose hardware, a general-purpose personal computer that can execute various kinds of functions, having various kinds of programs installed thereinto, or the like, for example.

Figure 8:
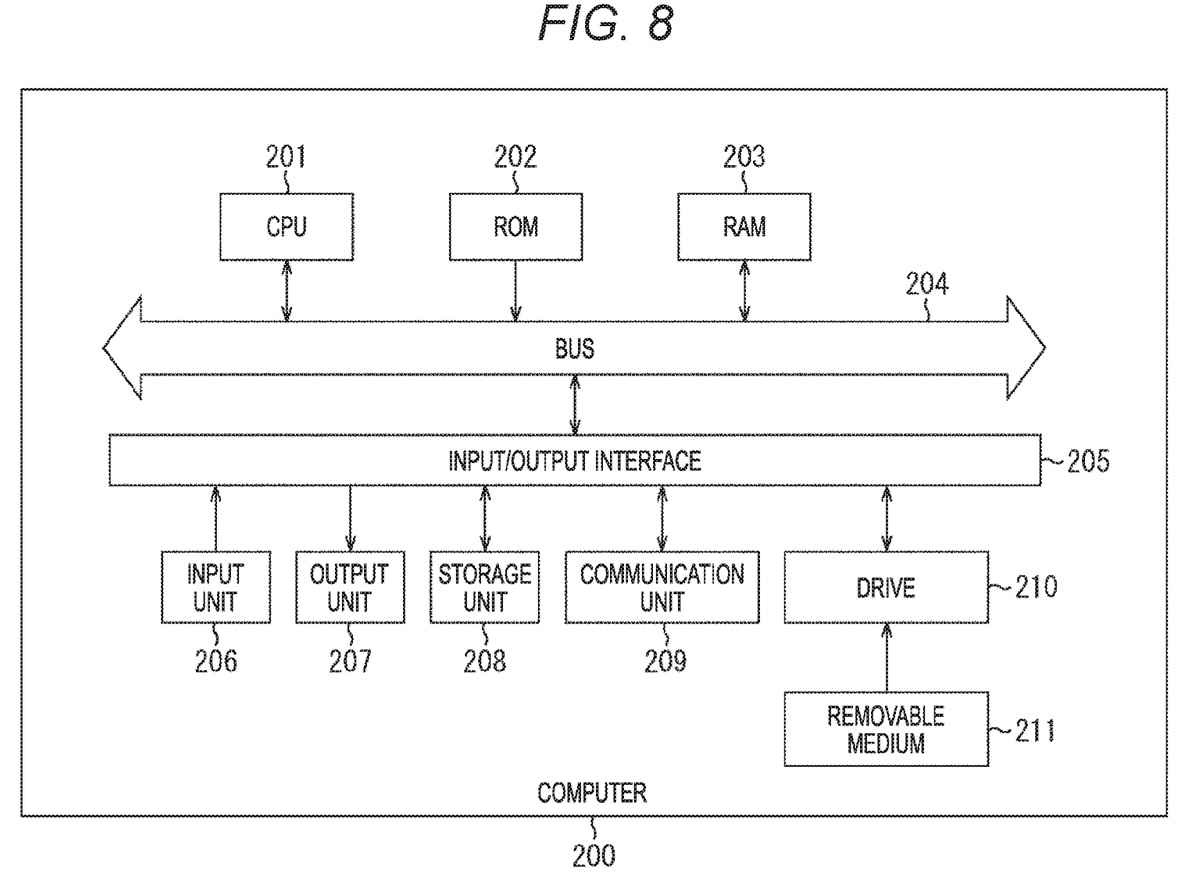
FIG. 8 is a block diagram showing an example configuration of a general-purpose computer.

FIG. 8 is a block diagram showing an example configuration of the hardware of a computer that performs the above described series of processes in accordance with a program.

In the computer, a central processing unit (CPU) 201, a read only memory (ROM) 202, and a random access memory (RAM) 203 are connected to one another by a bus 204.

An input/output interface 205 is further connected to the bus 204. An input unit 206, an output unit 207, a storage unit 208, a communication unit 209, and a drive 210 are connected to the input/output interface 205.

The input unit 206 is formed with a keyboard, a mouse, a microphone, and the like. The output unit 207 is formed with a display, a speaker, and the like. The storage unit 208 is formed with a hard disk, a nonvolatile memory, or the like. The communication unit 209 is formed with a network interface or the like. The drive 210 drives a removable medium 211, such as a magnetic disk, an optical disk, a magnetooptical disk, or a semiconductor memory.

In the computer having the above described configuration, the CPU 201 loads a program stored in the storage unit 208 into the RAM 203 via the input/output interface 205 and the bus 204, for example, and executes the program, so that the above described series of processes are performed.

The program to be executed by the computer (the CPU 201) may be recorded on the removable medium 211 as a packaged medium or the like to be provided, for example. Alternatively, the program can be provided via a wired or wireless transmission medium, such as a local area network, the Internet, or digital satellite broadcasting.

In the computer, the program can be installed into the storage unit 208 via the input/output interface 205 when the removable medium 211 is mounted on the drive 210. The program can also be received by the communication unit 209 via a wired or wireless transmission medium, and be installed into the storage unit 208. Also, the program may be installed beforehand into the ROM 202 or the storage unit 208.

Note that the program to be executed by the computer may be a program for performing processes in chronological order in accordance with the sequence described in this specification, or may be a program for performing processes in parallel or performing a process when necessary, such as when there is a call.

Note that embodiments of the present disclosure are not limited to the above described embodiment, and various modifications may be made to the embodiment without departing from the scope of the present disclosure.

The present disclosure may be embodied in the configurations described below.

(1)

An information processing device including:

a moving object detection unit that detects a moving object in a captured image;

a stay area information holding unit that holds stay area information indicating a position of the moving object detected in the captured image;

a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map.

(2)

The information processing device according to (1), in which the stay frequency map generation unit extracts, from time-series stay area information being held, the stay area information corresponding to a predetermined time period determined in accordance with time information, and generates a stay frequency map by combining the extracted stay area information.

(3)

The information processing device according to (2), in which the time information includes a time schedule of a facility in which the information processing device is being used.

(4)

The information processing device according to (1) or (2), in which the stay frequency map generation unit extracts, from time-series stay area information being held, the stay area information corresponding to a predetermined time period determined in accordance with moving object information about the moving object, and generates a stay frequency map by combining the extracted stay area information.

(5)

The information processing device according to (4), in which the moving object information includes at least one of a respiration rate or a heart rate of a living body as the moving object.

(6)

The information processing device according to (4) or (5), further including a moving object information acquisition unit that acquires the moving object information by sensing an imaging range of the captured image.

(7)

The information processing device according to any of (1) to (6), further including an imaging unit that forms the captured image.

(8)

The information processing device according to any of (1) to (7), further including an illumination unit that illuminates an imaging range of the captured image with visible light and/or invisible light.

(9)

The information processing device according to any of (1) to (8), further including a behavior recognition unit that performs behavior recognition on the moving object, in accordance with the captured image and the specific region in the captured image.

(10)

The information processing device according to (9), further including a reporting unit that reports a result of recognition of a behavior of the moving object.

(11)

An information processing method implemented in an information processing device, the information processing method causing the information processing device to carry out:

a moving object detection step of detecting a moving object in a captured image;

a stay area information holding step of holding stay area information indicating a position of the moving object detected in the captured image;

a stay frequency map generation step of extracting the stay area information corresponding to a predetermined time period from time-series stay area information being held, and generating a stay frequency map by combining the extracted stay area information; and a specific region determination step of determining a specific region having a high stay frequency regarding the moving object, in accordance with the generated stay frequency map.

(12)

A program for causing a computer to function as:

a moving object detection unit that detects a moving object in a captured image;

a stay area information holding unit that holds stay area information indicating a position of the moving object detected in the captured image;

a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map.

(13)

A watching system including:

an imaging unit that forms a captured image;

an illumination unit that illuminates an imaging range of the imaging unit with visible light and/or invisible light;

a moving object detection unit that detects a moving object in a captured image;

a stay area information holding unit that holds stay area information indicating a position of the moving object detected in the captured image;

a stay frequency map generation unit that extracts the stay area information corresponding to a predetermined time period from time-series stay area information being held, and generates a stay frequency map by combining the extracted stay area information; and a specific region determination unit that determines a specific region having a high stay frequency regarding the moving object, in accordance with the generated stay frequency map.

REFERENCE SIGNS LIST

10 Watching system
11 Imaging unit
12 Illumination unit
13 Image processing unit
14 Moving object extraction/tracking unit
15 Stay area determination unit
16 Stay area database
17 Specific region determination unit
18 Specific region database
19 Object information sensing unit
20 Information processing unit
21 Object information database
22 Behavior recognition unit
23 Report determination unit
24 Network control unit
25 Video database
200 Computer
201 CPU

The invention claimed is:

1. An information processing device comprising:
a moving object detection unit that detects a moving object in a captured image;
a stay area information holding unit that holds stay area information indicating a position of the moving object detected in the captured image;
a stay frequency map generation unit that extracts the stay area information corresponding to a predetermined time period from time-series stay area information, and generates a stay frequency map by combining the extracted stay area information; and
a specific region determination unit that determines a specific region having a high stay frequency regarding the moving object, in accordance with the generated stay frequency map.

2. The information processing device according to claim 1, wherein the predetermined time period is determined in accordance with time information.

3. The information processing device according to claim 2, wherein the time information includes a time schedule of a facility in which the information processing device is being used.

4. The information processing device according to claim 2, wherein the predetermined time period is determined in accordance with moving object information about the moving object.

5. The information processing device according to claim 4, wherein the moving object information includes at least one of a respiration rate or a heart rate of a living body as the moving object.

6. The information processing device according to claim 5, further comprising
a moving object information acquisition unit that acquires the moving object information by sensing an imaging range of the captured image.

7. The information processing device according to claim 2, further comprising
an imaging unit that forms the captured image.

8. The information processing device according to claim 2, further comprising
an illumination unit that illuminates an imaging range of the captured image with visible light and/or invisible light.

9. The information processing device according to claim 2, further comprising
a behavior recognition unit that performs behavior recognition on the moving object, in accordance with the captured image and the specific region in the captured image.

10. The information processing device according to claim 9, further comprising
a reporting unit that reports a result of recognition of a behavior of the moving object.

11. An information processing method implemented in an information processing device, the method comprising:
detecting a moving object in a captured image;
holding stay area information indicating a position of the moving object detected in the captured image;
extracting the stay area information corresponding to a predetermined time period from time-series stay area information, and generating a stay frequency map by combining the extracted stay area information; and
determining a specific region having a high stay frequency regarding the moving object, in accordance with the generated stay frequency map.

12. A non-transitory computer readable medium storing program code executable by a computer to perform operations comprising:
detecting a moving object in a captured image;
holding stay area information indicating a position of the moving object detected in the captured image;
extracting the stay area information corresponding to a predetermined time period from time-series stay area information, and generating a stay frequency map by combining the extracted stay area information; and
determining a specific region having a high stay frequency regarding the moving object, in accordance with the generated stay frequency map.

13. A watching system including:
an imager configured to form a captured image;
a light source configured to illuminate an imaging range of the imaging unit with visible light and/or invisible light;
a memory storing program code; and
a processor configured to execute the program code to perform operations comprising:
detecting a moving object in a captured image,
holding stay area information indicating a position of the moving object detected in the captured image,
extracting the stay area information corresponding to a predetermined time period from time-series stay area information, and generating a stay frequency map by combining the extracted stay area information, and
determining a specific region having a high stay frequency regarding the moving object, in accordance with the generated stay frequency map.

14. The method according to claim 11, wherein the predetermined time period is determined in accordance with time information.

15. The method according to claim 14, wherein the time information includes a time schedule of a facility in which the information processing device is being used.

16. The method according to claim 14, wherein the predetermined time period is determined in accordance with moving object information about the moving object.

17. The non-transitory computer readable medium according to claim 12, wherein the predetermined time period is determined in accordance with time information.

18. The non-transitory computer readable medium according to claim 17, wherein the time information includes a time schedule of a facility in which the information processing device is being used.

19. The non-transitory computer readable medium according to claim 17, wherein the predetermined time period is determined in accordance with moving object information about the moving object.

20. The system according to claim 13, wherein the predetermined time period is determined in accordance with time information.

21. The system according to claim 20, wherein the time information includes a time schedule of a facility in which the information processing device is being used.

22. The system according to claim 20, wherein the predetermined time period is determined in accordance with moving object information about the moving object.

* * * * *